(12) United States Patent
Shiota et al.

(10) Patent No.: US 9,271,995 B2
(45) Date of Patent: *Mar. 1, 2016

(54) AGENT FOR AMELIORATING BRAIN HYPOFUNCTION

(71) Applicants: The University of Tokyo, Tokyo (JP); School Corporation, Azabu Veterinary Medicine Educational Institution, Sagamihara-shi (JP)

(72) Inventors: Kunio Shiota, Tokyo (JP); Masayoshi Kuwahara, Tokyo (JP); Takefumi Kikusui, Sagamihara (JP); Shintaro Yagi, Tokyo (JP)

(73) Assignees: The University of Tokyo, Tokyo (JP); School Corporation, Azabu Veterinary Medicine Educational Institution, Sagamihara (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/662,195

(22) Filed: Mar. 18, 2015

(65) Prior Publication Data

US 2015/0190414 A1 Jul. 9, 2015

Related U.S. Application Data

(63) Continuation of application No. 13/035,717, filed on Feb. 25, 2011, now Pat. No. 8,987,232, which is a continuation-in-part of application No. PCT/JP2009/065438, filed on Sep. 3, 2009.

(30) Foreign Application Priority Data

Sep. 4, 2008 (JP) ................................. 2008-226858
Feb. 26, 2010 (JP) ................................. 2010-043308

(51) Int. Cl.
 *A61K 31/7008* (2006.01)
(52) U.S. Cl.
 CPC .................................. *A61K 31/7008* (2013.01)
(58) Field of Classification Search
 CPC .................................................. A61K 31/7008
 USPC ........................................................ 514/23
 See application file for complete search history.

(56) References Cited

U.S. PATENT DOCUMENTS

| 6,274,568 | B1 * | 8/2001 | Schnaar ................. C07H 13/04 435/7.1 |
| 6,432,989 | B1 | 8/2002 | Chen |
| 8,987,232 | B2 * | 3/2015 | Shiota ................ A61K 31/7008 514/62 |
| 2004/0258645 | A1 | 12/2004 | Trejo et al. |
| 2005/0123500 | A1 | 6/2005 | Trejo et al. |
| 2010/0249047 | A1 | 9/2010 | Huizing et al. |

FOREIGN PATENT DOCUMENTS

| DE | 3935906 A1 | 5/1991 |
| JP | H09-301874 A | 11/1997 |
| JP | H10-182685 A | 7/1998 |
| JP | 2001-078794 A | 3/2001 |
| JP | 2006-524187 A | 10/2006 |
| WO | WO 2004/068970 A2 | 8/2004 |
| WO | WO 2008/150477 A2 | 12/2008 |

OTHER PUBLICATIONS

Olson et al, Brain 2000, 123(2), 331-39.*
The Merck Manual 1992, 16th Ed., p. 1403-05.*
Kasparova et al., *Neurochemical Research*, 26(8/9): 1079-1084 (2001).
Kutty et al., *Toxicol. Appl. Pharmacol.*, 107(2): 377-388 (1991).
Merck Research Laboratories, The Merck Manual of Diagnosis and Therapy, 16th Ed., pp. 1403-1405 (1992).
Nomura et al., *Neurosci. Lett.*, 549: 163-167 (2013).
Olson et al., *Brain*, 123(2): 331-339 (2000).
Pifl et al., *The Journal of Neuroscience*, 13(10): 4246-4253 (1993).
Suwanakitch et al., *ScienceAsia*, 34: 035-042 (2008).
Japanese Patent Office, International Search Report in International Patent Application No. PCT/JP2009/065438 (Nov. 10, 2009).
Japanese Patent Office, International Preliminary Report on Patentability in International Patent Application No. PCT/JP2009/065438 (Apr. 12, 2011).

* cited by examiner

*Primary Examiner* — Ganapathy Krishnan
(74) *Attorney, Agent, or Firm* — Leydig, Voit & Mayer, Ltd.

(57) ABSTRACT

Provided are effective and highly safe agents, medicaments and the like for ameliorating various disorders caused by brain hypofunction. Also provided is a preventing or ameliorating agent for brain hypofunction containing N-acetyl-D-mannosamine, a pharmaceutical composition for preventing, ameliorating or treating disorders due to brain hypofunction, containing an effective amount of N-acetyl-D-mannosamine and a pharmaceutically acceptable carrier, and a food comprising N-acetyl-D-mannosamine added thereto.

8 Claims, 8 Drawing Sheets

AGENT FOR AMELIORATING BRAIN HYPOFUNCTION

This application is a continuation of U.S. patent application Ser. No. 13/035,717, filed on Feb. 25, 2011, which is a continuation-in-part of International Patent Application No. PCT/JP2009/065438, filed on Sep. 3, 2009, which is incorporated by reference in its entirety herein, and which claims the benefit of Japanese Patent Application No. 2008-226858, filed on Sep. 4, 2008.

This application also claims the benefit of Japanese Patent Application No. 2010-043308, filed Feb. 26, 2010.

TECHNICAL FIELD

The present invention relates to an agent for ameliorating brain hypofunction, more specifically to pharmaceutical use applications of N-acetyl-D-mannosamine.

BACKGROUND ART

A large number of drugs are inducers of sleep. There are also many drugs exhibiting awakening action. However, these drugs pose problems of drug resistance and drug dependence in prolonged use. Additionally, these drugs do not improve "the quality of sleep" for the purpose of treating aging-related sleep disorders. Furthermore, no drugs are available that ameliorate learning and memory disorders that develop with aging. With the aging of the general population, the ratio of people suffering a quantitative or qualitative reduction in their sleep is increasing. Various cerebral disorders that develop due to aging-related brain hypofunction have major difficulties not only on patients, but also on society as a whole.

To date, central nervous stimulants and sleep-inducing drugs have been used for sleep disorders. Most of them target the neurotransmitter pathways, and many are short-time acting, though the persistency of action varies among different agents. Both central nervous stimulants and sleep-inducing drugs have a risk to cause adverse reactions such as dependence, habituation, and transient amnesia, many of which are designated narcotics by law.

Sleep, one of the most fundamental physiological functions of organisms, is essential for their survival. Although its physiological significance is still disputable, sleep is thought to be involved in higher brain functions such as recovery from psychosomatic fatigue and memory fixation and reconsolidation.

Based on electromyographic and electroencephalographic analyses, sleep can be divided into two stages: non-REM sleep, characterized by decreased brain function, and REM sleep, where brain function is active but skeletal muscles are relaxed. What is called deep sleep, slow wave sleep, belongs to non-REM sleep. Although the ratio of REM and non-REM sleep stages and the length of sleep differ among different biological species, REM sleep and slow wave sleep are also observed in mice and other non-human animals.

The REM sleep stage is thought to be particularly important to ensure that higher brain functions such as memory fixation and reconsolidation occur normally.

Sleep disorders are roughly divided into two categories: hypersomnia and asomnia. Typical conditions are narcolepsy in the former and insomnia in the latter. Caused by a broad range of factors, sleep disorders are induced in case of forced time shifts such as jet lags and shift work, or with stress due to overwork and the like. Meanwhile, many cases of sleep disorders accompany some other diseases; cardiac function abnormalities, obesity and the like are likely to lead to inadequate sleep. Sleep disorders also occur as adverse reactions to many drugs. For example, antipyretics, antiallergic remedies, gastrointestinal drugs such as H2 blockers induce drowsiness. Furthermore, brain function disorders, e.g., schizophrenia, bipolar disorders, Alzheimer's disease, Parkinson's disease are sometimes accompanied by sleep disorders.

In general, the quality and quantity of sleep decrease with age. Experiencing difficulty in falling asleep, early wakeups, diminished wake-sleep rhythms between day and night, decreased REM sleep, decreased slow wave sleep and the like, many people in their senescence are somewhat dissatisfied with their sleep. Furthermore, many prescribed drugs (for symptoms other than sleep-related ones) disturb sleep as adverse reactions, and most elderly people are on medication with one or more drugs prescribed; it is somewhat difficult to elucidate the causes of their complaints regarding sleep and take countermeasures. Described below are some currently available therapeutic drugs for sleep disorders.

Central Nervous Stimulants

Amphetamine or chemically synthesized stimulants with similar structure have long been used to suppress narcolepsy and daytime drowsiness in shift works. As an indirect adrenergic agonist, amphetamine potently stimulates the central nervous system by promoting the release of noradrenaline and dopamine, inhibiting their reuptake, and inhibiting monoamine oxidase (MAO). Its use is prohibited in Japan for the reason of adverse reactions in prolonged use or overuse. Modafinil is used in the US since it is unlikely to produce habituation and adverse reactions, although its action point remains unknown. Contained in foods, caffeine exhibits stimulatory action; it is thought to be safe when taken in appropriate amounts, but it causes mild dependency.

Sleep-Inducing Drugs

Commonly prescribed sleep-inducing drugs include brotizolam (Lendormin), triazolam (Halcion), flunitrazepam (Rohypnol), Silece, Amoban and the like; these act mainly on receptors of the inhibitory neurotransmitter GABA; adverse reactions such as motor disorders, memory disorders, drug dependence, and carryover effects are problematic in long-term use.

Drugs that are more effective on GABA-A receptors, e.g., zolpidem (Ambien), zaleplon (Sonata), zopiclone (Imovane), and eszopiclone (Lunesta), all decrease REM sleep to promote sleep onset, and are mostly effective in suppressing the transition from slow wave sleep to wakefulness. These sleep-inducing drugs are also effective as sedatives, and have been reported to produce unusual behavior as adverse reactions while the user is in an anti-wake state.

As such, the sleep-inducing drugs and central nervous stimulants act directly on the neurotransmitter pathway, so that their effects usually occur instantaneously; they must be taken just before expecting an effect (within several hours). Because the targeted neurotransmitter pathway is not associated exclusively with sleep, they cause serious disorders when taken in large amounts. Additionally, prolonged use leads to a reduction in the responsiveness of the neurotransmission pathway, which can cause drug dependence. Furthermore, the rebound phenomenon following drug discontinuation is considerable to the extent of likely habituation, thus increasing the risk of drug dependence.

Although melatonin is prescribed for mild cases of sleep disorders, especially for those due to a shift of circadian rhythm, it is not positively prescribed by specializing physicians because of a lack of difference in clinical efficacy compared with phototherapy.

N-acetyl-D-mannosamine, an isomer of N-acetyl-D-glucosamine, is known as, for example, a starting material for the enzymatic synthesis of sialic acid (N-acetyl-neuraminic acid), which serves as a medicament and a starting material for other medicaments. Also, N-acetyl-D-mannosamine permits enzymatic synthesis of sialic acid derivatives from derivatives thereof, hence an industrially important substance. In a known method of producing N-acetyl-D-mannosamine, the molar conversion yield of N-acetyl-mannosamine from N-acetyl-glucosamine in isomerizing the latter under alkaline conditions is increased by the addition of boric acid or borate (JP-A-HEI-10-182685). Another known method is such that sialic acid, as the substrate, is reacted with N-acetyl-neuraminate lyase to produce N-acetyl-D-mannosamine (JP-A-2001-78794). A method has been proposed wherein the acylated form of N-mannosamine is contacted with cells to regulate lectin binding to cell surfaces or to regulate the proliferation of nerve cells (U.S. Pat. No. 6,274,568).

N-acetyl-D-mannosamine is utilized as a starting material for the synthesis of sialic acid or an intermediate for medicaments. As the situation stands, however, it is not used as a final product in medicaments or foods. Furthermore, there is no knowledge that N-acetyl-D-mannosamine is effective in ameliorating brain hypofunction and in ameliorating sleep disorders.

SUMMARY OF THE INVENTION

Problems to be Solved by the Invention

The present invention has been developed in view of the above-described circumstances, and is directed to providing an effective and highly safe agent, medicament and the like for ameliorating various disorders caused by brain hypofunction.

Means of Solving the Problems

The present inventors extensively investigated to solve the above-described problems and, as a result, unexpectedly found that N-acetyl-D-mannosamine improves memory, significantly extends REM sleep time in the sleep rhythm, and normalizes the wake-sleep rhythm from its disturbance in animal experiments using old animals. The present inventors conducted further investigations, and have completed the present invention.

Accordingly, the present invention relates to the following:
[1] An agent for preventing or ameliorating a brain hypofunction comprising N-acetyl-D-mannosamine.
[2] The preventing or ameliorating agent according to [1] above, wherein the brain hypofunction is aging-related brain hypofunction.
[3] The preventing or ameliorating agent according to [1] or [2] above, wherein the agent is intended to prevent or ameliorate a disorder selected from the group consisting of sleep disorders, place memory disorders, object memory disorders, affective disorders and decrease in motor function.
[4] An agent for preventing or ameliorating a REM sleep disorder, comprising N-acetyl-D-mannosamine.
[5] The preventing or ameliorating agent according to any one of [1] to [4] above, wherein the agent is a medicament.
[6] The preventing or ameliorating agent according to any one of [1] to [4] above, wherein the agent is a functional health food or a food additive.
[7] A pharmaceutical composition for preventing, ameliorating or treating a disorder due to a brain hypofunction, comprising an effective amount of N-acetyl-D-mannosamine and a pharmaceutically acceptable carrier.
[8] The pharmaceutical composition according to [7] above, wherein the disorder is due to aging-related brain hypofunction.
[9] The pharmaceutical composition according to [7] or [8] above, wherein the disorder is selected from the group consisting of sleep disorders, place memory disorders, object memory disorders, affective disorders and decrease in motor function.
[10] A pharmaceutical composition for preventing, ameliorating or treating a REM sleep disorder, comprising an effective amount of N-acetyl-D-mannosamine and a pharmaceutically acceptable carrier.
[11] A food comprising N-acetyl-D-mannosamine added thereto.
[12] Use of N-acetyl-D-mannosamine for producing a medicament for preventing, ameliorating or treating a disorder due to a brain hypofunction.
[13] The use according to [12] above, wherein the disorder is due to aging-related brain hypofunction.
[14] The use according to [12] or [13] above, wherein the disorder is selected from the group consisting of sleep disorders, place memory disorders, object memory disorders, affective disorders and decrease in motor function.
[15] Use of N-acetyl-D-mannosamine for producing a medicament for preventing, ameliorating or treating a REM sleep disorder.
[16] A method of preventing, ameliorating or treating a disorder due to a brain hypofunction, comprising the step of administering an effective amount of N-acetyl-D-mannosamine to a subject in need thereof.
[17] The method according to [16] above, wherein the disorder is due to aging-related brain hypofunction.
[18] The method according to [16] above, wherein the disorder is selected from the group consisting of sleep disorders, place memory disorders, object memory disorders, affective disorders and decrease in motor function.
[19] A method of preventing, ameliorating or treating a REM sleep disorder, comprising the step of administering an effective amount of N-acetyl-D-mannosamine to a subject in need thereof.
[20] A method of preventing or ameliorating brain hypofunction, comprising the step of allowing an effective amount of N-acetyl-D-mannosamine to be taken by a subject in need thereof.
[21] The method according to [20] above, wherein the brain hypofunction is aging-related brain hypofunction.
[22] The method according to [20] or [21] above, wherein the method is intended to prevent or ameliorate a disorder selected from the group consisting of sleep disorders, place memory disorders, object memory disorders, affective disorders and decrease in motor function.
[23] A method of preventing or ameliorating a REM sleep disorder, comprising the step of allowing an effective amount of N-acetyl-D-mannosamine to be taken by a subject in need thereof.
[24] A commercial package comprising the preventing or ameliorating agent according to any one of [1] to [4] and [6] above, and a printed matter bearing an explanation concerning the preventing or ameliorating agent, stating that the preventing or ameliorating agent can be used, or should be used, to prevent or ameliorate a brain hypofunction.

[25] A commercial package comprising the pharmaceutical composition according to any one of [7] to [10] above, and a printed matter bearing an explanation concerning the pharmaceutical composition, stating that the pharmaceutical composition can be used, or should be used, to prevent, ameliorate or treat a disorder due to a brain hypofunction.

Effect of the Invention

According to the preventing or ameliorating agent for brain hypofunction of the present invention, it is possible to improve metabolism by activating various cells in a living organism, to thereby delay decrease in brain function or recover from the decreased brain function. This effect is believed to occur since the active ingredient N-acetyl-D-mannosamine is supplied as a promoter of sugar metabolism into individual cells and eventually improves brain function. Therefore, the pharmaceutical composition of the present invention, which comprises N-acetyl-D-mannosamine as an active ingredient, is capable of preventing, ameliorating or treating various central diseases that develop with brain hypofunction (dementia, dementia of Alzheimer type, dementia with Lewy bodies, frontotemporal lobar dementia, sleep disorders, insomnia, arousal disorders, circadian rhythm sleep disorders, delayed sleep phase syndrome, advanced sleep phase syndrome) and the like by acting to improve the metabolism in the whole body of a living organism. The food of the present invention is safe because it is based on the monosaccharide N-acetyl-D-mannosamine; when taken routinely, it is expected to prevent or ameliorate brain hypofunction.

The preventing or ameliorating agent of the present invention for sleep disorders, particularly for REM sleep disorders, makes it possible to extend REM sleep time that has once decreased due to aging and the like, to improve the quality and quantity of sleep, and concurrently to restore the sleep wake rhythmic cycle between day and night. This effect begins to be evident on day 2 after the start of administration of the ingredient N-acetyl-D-mannosamine, but the sleep induction effect does not appear soon after the start of administration as with conventional sleep-inducing drugs. Additionally, the improvements of the quality of sleep and the like last for a given period (1 to 2 days) even after completion of administration, but then they disappear. Since administration with free access to water is also effective, the method of formulation is not limited. Nor is there any limitation on the time the formulation is taken because the sleep-wake rhythm does not shift after ingestion. Hence, the preventing or ameliorating agent of the present invention for sleep disorders, particularly for REM sleep disorders, exhibits effects that are completely different from those of conventional sleep-inducing drugs and central nervous stimulants; therefore, it is evident that the preventing or ameliorating agent of the present invention exhibits its pharmacological effect by an action mechanism different from that for conventional drugs that target the neurotransmitter pathway. The pharmaceutical composition of the present invention and the food of the present invention, which comprise N-acetyl-D-mannosamine as an active ingredient, are safe because they are based on N-acetyl-D-mannosamine, a monosaccharide occurring in living organisms by nature, and are expected to prevent or ameliorate sleep disorders when taken routinely.

BRIEF DESCRIPTION OF THE DRAWINGS

In FIG. 5A, the vertical axis indicates the ratio of wake time in a day (24 hours). In FIG. 5B, the vertical axis indicates the ratio of REM sleep time in a day. In FIG. 5C, the vertical axis indicates the ratio of slow wave sleep time in a day.

In FIG. 8A, the vertical axis indicates the ratio of wake time in a day (24 hours). In FIG. 8B, the vertical axis indicates the ratio of REM sleep time in a day. In FIG. 8C, the vertical axis indicates the ratio of slow wave sleep time in a day.

MODES FOR EMBODYING THE INVENTION

Figure 1:
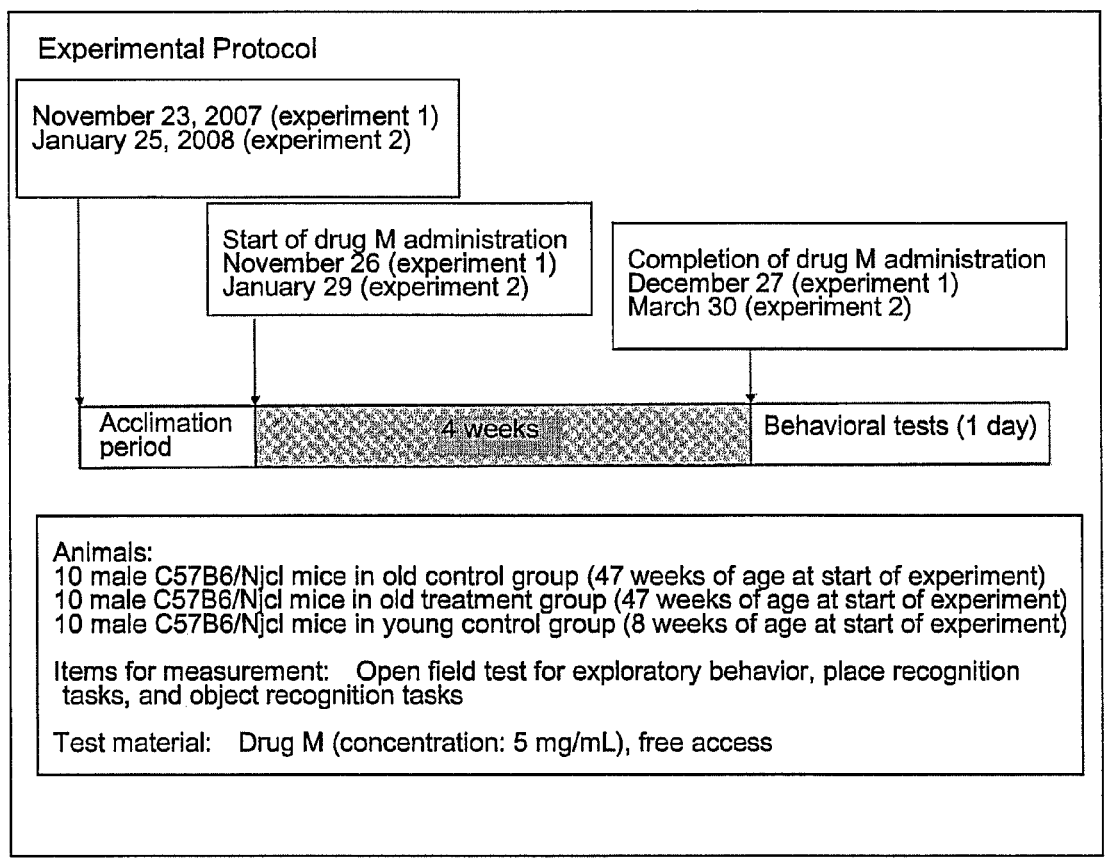
FIG. 1 shows the protocol for object and place recognition task experiments, wherein drug M indicates ManNAc.

The preventing or ameliorating agent for brain hypofunction of the present invention (hereinafter sometimes simply referred to as "agent") comprises N-acetyl-D-mannosamine.

In the present invention, N-acetyl-D-mannosamine (hereinafter sometimes abbreviated ManNAc) is the N-acetyl-form of D-mannosamine represented by the formula (I):

In the present invention, the term N-acetyl-D-mannosamine is not limited to the simple substance represented by the formula (I) above, but encompasses the salts thereof, solvates thereof, and derivatives thereof.

Salts of N-acetyl-D-mannosamine include pharmacologically acceptable salts, e.g., salts with inorganic acids, salts with organic acids, salts with basic or acidic amino acids and the like.

Examples of salts with inorganic acids include salts with hydrochloric acid, hydrobromic acid, nitric acid, sulfuric acid, phosphoric acid and the like.

Examples of salts with organic acids include salts with benzoic acid, formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Examples of salts with basic amino acids include salts with arginine, lysine, ornithine and the like; examples of suitable salts with acidic amino acids include salts with aspartic acid, glutamic acid and the like.

Solvates of N-acetyl-D-mannosamine preferably include hydrates (e.g., monohydrate, dihydrate and the like), ethanolates and the like.

Derivatives of N-acetyl-D-mannosamine include those represented by the formula (II) below.

[wherein each of $R^1$, $R^2$, $R^3$, $R^4$ and $R^5$ independently represents hydrogen (H), $R^6$, —C(=O) $R^6$, —C(=O)$OR^6$, or —C(=O) $NR^6R^7$; $R^6$ represents an optionally substituted $C_1$-$C_7$ linear or cyclic hydrocarbon; $R^7$ represents hydrogen (H), an optionally substituted $C_1$-$C_7$ linear or cyclic hydrocarbon.]

Useful substituents are F, Cl, and Br.

The N-acetyl-D-mannosamine used may be a commercial product, or may be prepared by a method known per se. Useful methods of producing N-acetyl-D-mannosamine include, but are not limited to, a method involving isomerizing N-acetyl-glucosamine under alkaline conditions (JP-A-HEI-10-182685) and a method involving a reaction of sialic acid as the substrate with N-acetyl-neuraminate lyase (JP-A-2001-78794).

In the present invention, "brain hypofunction" refers to a state where the function of the brain is subnormal due to various factors in the processes from animal genesis to death, compared with the brain function of the same animal in the mature stage. A representative cause of brain hypofunction is senescence; other causal factors include, but, because of the involvement of a variety of factors in individual animals, are not limited to, stress, the environment, hereditary diseases, organic disorders and the like. Although the brain maturity stage varies depending on the species of animal, and cannot be generalized, adulthood may usually serve as an indicator. The stage occurs at 15 to 30 years of age for humans and 7 to 20 weeks of age for mice.

The brain hypofunction to which the present invention is applied is preferably aging-related brain hypofunction; brain hypofunction manifests itself in the form of sleep disorders, place memory disorders, object memory disorders, affective disorders, decrease in motor function and the like.

Sleep disorders include sleep volume reductions and sleep quality reductions, the former manifesting themselves as increased sleep onset time, inadequate sleep time due to premature arousal and the like, and the latter developing as symptoms such as bedtime shifts, decreased deep sleep (non-REM sleep), sleep interruptions due to premature arousal, and naps in active time zones. Sleep disorders occur irrespective of the patient's age; especially the quality of sleep decreases with aging. A diagnosis is made by a test consisting of a plurality of inquiries, and is established by electroencephalography or by polysomnography, which measures multiple parameters, including electroencephalograms. Diagnoses can be classified according to internationally recognized criteria (The International Classification of Sleep Disorder, ICSD).

In the present invention, "REM sleep" refers to a state of sleep characterized by active brain function and relaxed skeletal muscles. Whether a living organism is in the REM sleep stage can be determined by analyzing electromyograms (EMG) or electroencephalograms (EEG). The REM sleep stage can also be identified by observing the rapid movement of eyeballs and increased heart rates. Meanwhile, "non-REM sleep" refers to a state of sleep characterized by suppressed brain function. Non-REM sleep can also be classified into four categories, from stage 1 (light sleep) to stage 4 (deep sleep); it is said that the transition to REM sleep occurs in stage 2.

In the present invention, "a REM sleep disorder" refers to a poor or bad condition in a living organism due to a REM sleep time reduction associated with aging or another reason. REM sleep disorders can become direct or indirect causal factors for, for example, insomnia, arousal disorders, circadian rhythm aberrations, metabolic or gastrointestinal disorders such as anorexia and weight loss, sensations of fatigue such as generalized lassitude and fatigability, cardiovascular disorders such as hypertension and heart failure, and central functional disorders such as of cognitive function and learning ability. In the present invention, these symptoms or conditions can be the subjects of prevention, amelioration or treatment.

Figure 2:
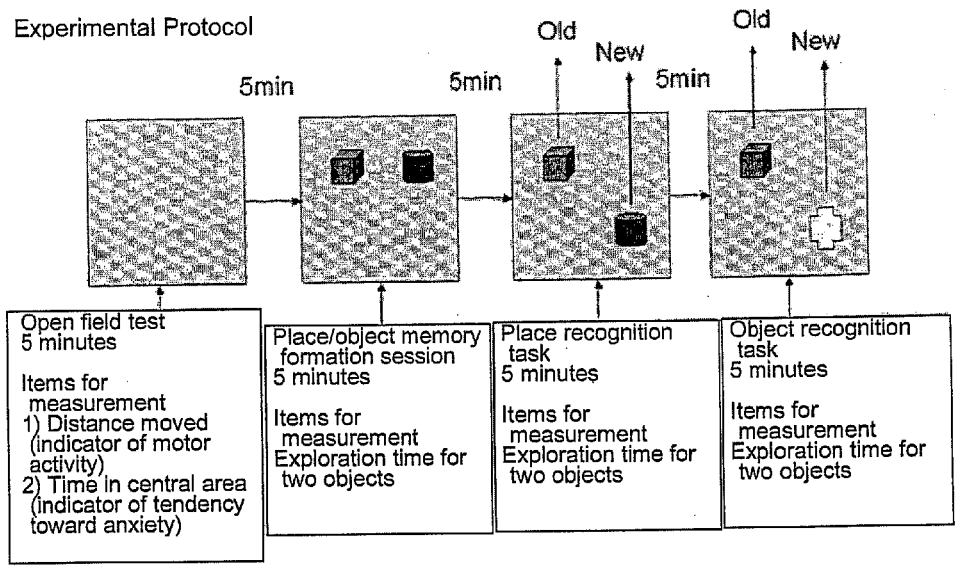
FIG. 2 shows the items for measurement in the object and place recognition task experiments.

A disorder of place memory refers to a disturbance of the recognition of the spacial position of self at a given time point, a disturbance of recognition memory for a place to which the subject has ever been and the like. A disorder of object memory refers to a disturbance of the recognition of an object perceived by contact and the like, a disorder of memorizing the experience and the like. These memory disorders can be measured by, for example, the place recognition task and object recognition task shown in Example 1 and FIG. 2.

Specifically, the agent of the present invention can be administered or taken for the purpose of preventing or ameliorating a disorder selected from the group consisting of the aforementioned sleep disorders (particularly REM sleep disorders), insomnia, arousal disorders, circadian rhythm sleep disorders, delayed sleep phase syndrome, advanced sleep phase syndrome, place memory disorders, object memory disorders, dementia, dementia of Alzheimer type, dementia with Lewy bodies and frontotemporal lobar dementia.

For these purposes, the agent of the present invention can be used as a medicament or functional health food or food additive in the form of N-acetyl-D-mannosamine, alone or after being blended with excipients (e.g., lactose, sucrose, starch, cyclodextrin and the like), sometimes further blended with flavors, dyes, seasoning agents, stabilizers, preservatives and the like, into tablets, pills, granules, fine granules, powders, pellets, capsules, solutions, emulsions, suspension, syrups, troches and the like. The agent of the present invention can also be used as a research reagent.

The amount of N-acetyl-D-mannosamine contained in the agent of the present invention is not particularly limited, as far as the effect of the present invention is obtained; the amount is normally 0.0001% to 100% by weight, preferably 0.001% to 99.9% by weight.

The present invention also provides a pharmaceutical composition for preventing, ameliorating or treating a disorder due to brain hypofunction, comprising an effective amount of N-acetyl-D-mannosamine and a pharmaceutically acceptable carrier.

Examples of pharmaceutically acceptable carriers include, but are not limited to, excipients (e.g., lactose, sucrose, dextrin, hydroxypropylcellulose, polyvinylpyrrolidone and the like), disintegrants (e.g., starch, carboxymethylcellulose and the like), lubricants (e.g., magnesium stearate and the like), surfactants (e.g., sodium lauryl sulfate and the like), solvents (e.g., water, saline, soybean oil and the like), preservatives (e.g., p-hydroxybenzoate and the like) and the like.

The effective amount of N-acetyl-D-mannosamine is not particularly limited, as far as an effect as a medicament is exhibited, and the amount is normally 0.0001% to 99.5% by weight, preferably 0.001% to 99.0% by weight.

The disorder to be prevented, ameliorated or treated with the pharmaceutical composition of the present invention is due to a brain hypofunction, preferably aging-related brain hypofunction. Disorders due to brain hypofunction include sleep disorders, especially those accompanied by REM sleep attenuation (herein, simply referred to as "REM sleep disorders"), place memory disorders, object memory disorders, dementia, dementia of Alzheimer type, dementia with Lewy bodies, frontotemporal lobar dementia and the like. The REM sleep disorders are preferably spontaneously developing sleep disorders that accompany senile aging and the like, including Alzheimer's disease, REM sleep behavioral disorders, narcolepsy, sleep-wake transition disorders and the like.

From another viewpoint, animals have individual differences; disorders due to brain hypofunction develop as a broad range of symptoms, and can sometimes be classified or diagnosed as particular diseases. Therefore, the pharmaceutical composition of the present invention can also be used to prevent, ameliorate or treat, for example, schizophrenia (preferably late-onset schizophrenia), Alzheimer's disease (preferably senile Alzheimer's disease), depression, dementia, dementia of Alzheimer type, dementia with Lewy bodies, frontotemporal lobar dementia, sleep disorders, insomnia, arousal disorders, circadian rhythm sleep disorders, delayed sleep phase syndrome, advanced sleep phase syndrome and the like.

The agent or pharmaceutical composition of the present invention can be safely administered to mammals (e.g., mice, rats, rabbits, cats, dogs, bovines, horses, monkeys, humans) orally or non-orally.

The present invention provides a food comprising N-acetyl-D-mannosamine added thereto.

The "food" of the present invention means any food in the general sense, and includes general foods, including what are called health foods, as well as functional health foods such as foods for specified health uses and foods with nutrient function claims, specified in the functional health food system by Japan's Ministry of Health, Labor and Welfare; nutritional supplements, animal feeds and the like are also encompassed in the scope of the food of the present invention.

In food use applications, N-acetyl-D-mannosamine can be used as contained in, for example, general foods (including what are called health foods) such as bread and confectionery. It is also possible to prepare N-acetyl-D-mannosamine, along with excipients (e.g., lactose, sucrose, starch and the like), sometimes further with flavors, dyes and the like, into preparations such as tablets, pills, granules, fine granules, powders, pellets, capsules, solutions, emulsions, suspensions, syrups and troches, and used as functional health foods such as foods for specified health uses and foods with nutrient function claims, or nutritional supplements. The food of the present invention is also applicable for feed applications, and can be taken or administered as added to ordinary feeds in poultry, farm animals and the like.

When taken as a food or feed, approximate figures of the number of times the food or feed is taken per day and the amount taken per time are calculated to define the daily intake amount, and the amount of N-acetyl-D-mannosamine contained in the daily intake amount of the food or feed is determined. The amount of N-acetyl-D-mannosamine contained can be determined on the basis of the doses described below.

The agent of the present invention can also be provided as a commercial package also comprising a printed matter bearing an explanation concerning the preventing or ameliorating agent, stating that the agent can be used, or should be used, to prevent or ameliorate brain hypofunction.

The pharmaceutical composition of the present invention can also be provided as a commercial package further comprising a printed matter bearing an explanation concerning the pharmaceutical composition, stating that the pharmaceutical composition can be used, or should be used, to prevent, ameliorate or treat disorders due to brain hypofunction.

To allow the N-acetyl-D-mannosamine contained to exhibit its biological action effectively, the food of the present invention is preferably used as a food for specified health uses or a food with nutrient function claims. In that situation, it is recommended that the product be labeled with the statement "to be used to prevent or ameliorate brain hypofunction", "improve the quality of sleep and wake-up", and "well-organize daily activities".

The amount of the agent, food or pharmaceutical composition of the present invention taken or administered varies depending on the recipient's age, body weight and health status, and cannot be generalized. For example, it is preferable that 0.1 to 10 g, preferably 0.2 g to 7 g, calculated as N-acetyl-D-mannosamine, be taken or eaten per day for an adult in one to several divided doses, usually in the form of a food for the purpose of maintaining and enhancing health or preventing or ameliorating brain hypofunction, and usually in the form of a medicament or food for the purpose of treating a disorder due to brain hypofunction or restoring health.

The dosage and administration of the medicament (agent or pharmaceutical composition) of the present invention is not particularly limited, as far as the route of administration ensures a preventive and therapeutic effect on the above-described disorders or diseases. For example, the same can be administered by parenteral administration (intravenous administration, intramuscular administration, direct administration into tissue, intranasal administration, intradermal administration, intramedullary administration and the like) or oral administration. For human application, in particular, the medicament of the present invention can be administered by intravenous, intramuscular or oral administration. There is no limitation on the dosage form; the medicament of the present invention can be administered as various dosage forms, e.g., oral formulations (granules, powders, tablets, capsules, syrups, emulsions, suspensions and the like), injections, drip infusions, external formulations (nasal preparations, transdermal preparations, ointments and the like).

The present invention also provides a use of N-acetyl-D-mannosamine for producing a medicament for preventing, ameliorating or treating brain hypofunction. Specifically, the present invention provides a method of producing a medicament for preventing, ameliorating or treating brain hypofunction using N-acetyl-D-mannosamine.

For producing the medicament of the present invention, methods known per se in the field of drug formulation can be used without limitations.

Contained at very low abundance in human cells as an intermediate, N-acetyl-D-mannosamine has no toxicities (e.g., acute toxicity, chronic toxicity, genotoxicity, reproductive toxicity, cardiac toxicity, drug interactions, carcinogenicity), and is believed to be highly safe in humans.

The agent, pharmaceutical composition or food of the present invention exhibits the following effects as shown in Examples.

(1) Improve ageing-related place memory and object memory to ameliorate aging-related brain hypofunction.
(2) Prolongs REM sleep and wake times significantly and inversely shortens non-REM sleep (slow wave sleep) time to maintain the sleep-wake rhythm at young ages.
(3) Suppress aging-related reductions of the quality of sleep, potentiates wakeful activities, and improves the quality of sleep.

EXAMPLES

The present invention is hereinafter described more specifically by means of the following Examples. However, the Examples only represent typical cases, and are variously modifiable, as far as the technical concept of the invention is not deviated from.

Example 1

Recovery from Brain Functional Disorders Such as Aging-Related Deteriorations of Object Memory and Place Memory Using ManNAc 1) Object and place recognition task experiments were performed on male C57BL6/Njcl mice in three groups. Outline of the experiments is shown in FIG. 1.

Old control group: Old mice (reared from 47 to 66 weeks of age, n=10) were allowed to drink tap water ad libitum.

Old ManNAc recipient group: Old mice (reared from 47 to 66 weeks of age, n=10) were allowed to drink tap water with ManNAc (5 mg/ml) dissolved therein ad libitum.

Young control group: Young mice (reared from 8 to 18 weeks of age, n=10) were allowed to drink tap water ad libitum.

2) Experimental procedures: An open field test was performed to examine the tendency toward anxiety and locomotor activity, and this was followed by place recognition task and object recognition task in accordance with conventional methods (see FIG. 2).

Figure 3:
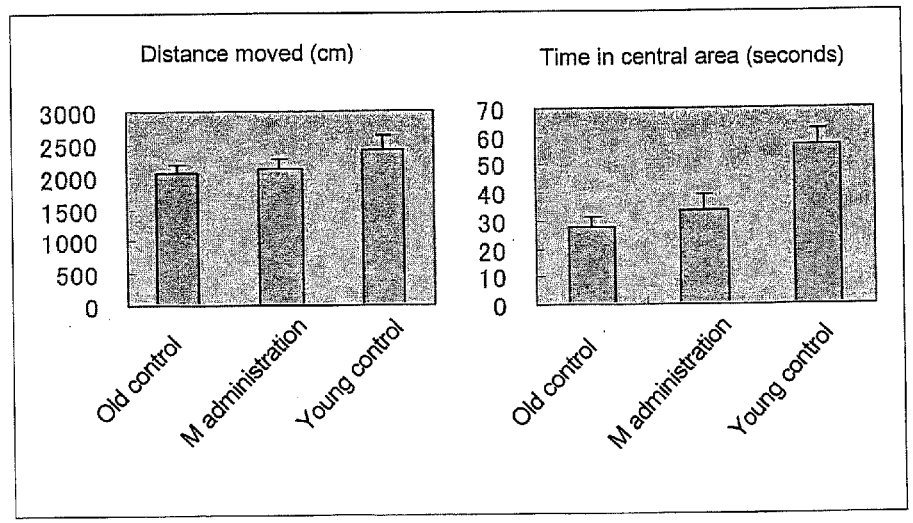
FIG. 3 is a graphic representation of the results of an open field test to compare old mice and young mice in terms of distance moved and time in central area in an unfamiliar open field.
Figure 4:
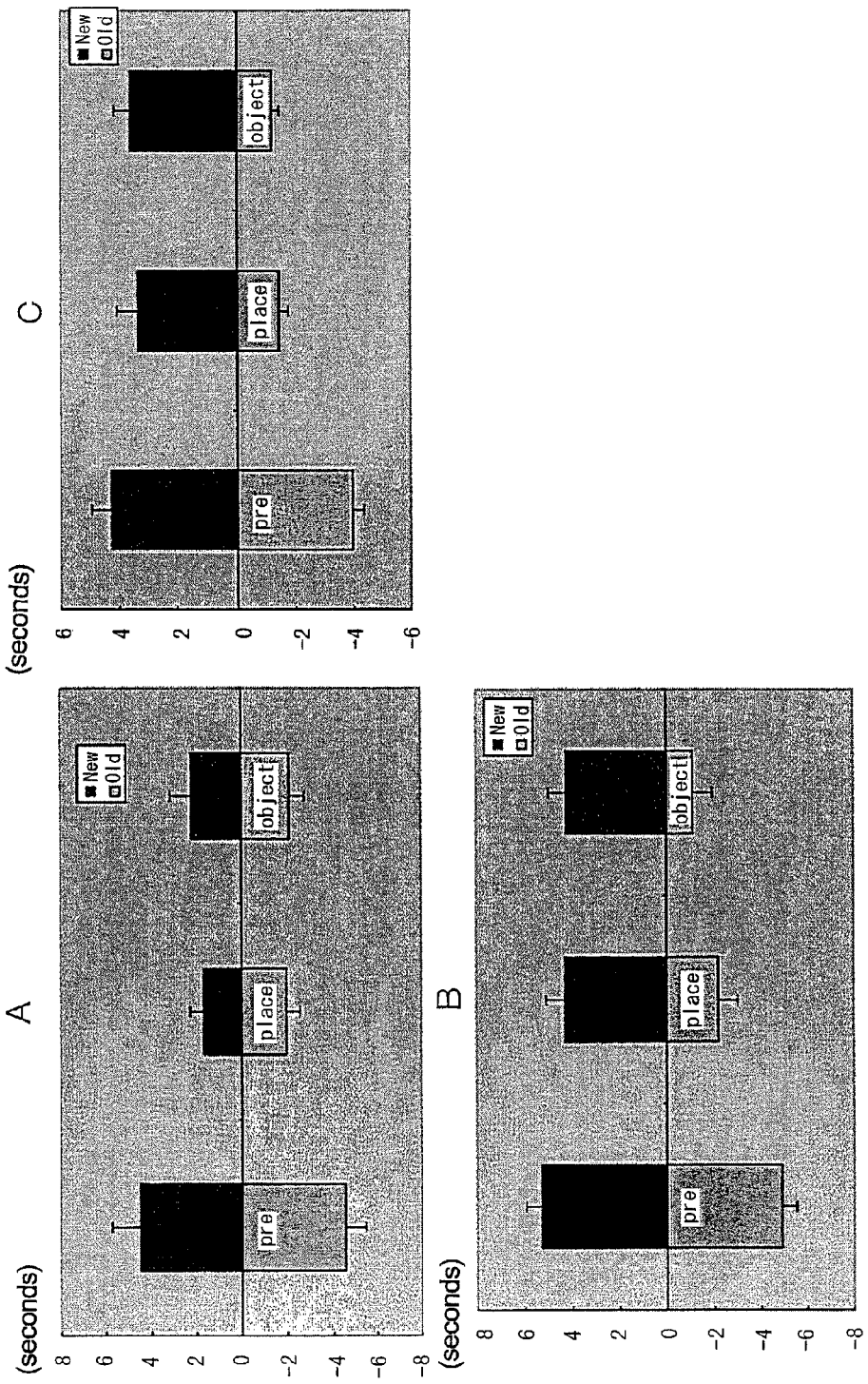
FIG. 4 is a graphic representation of the results of object and place recognition tasks.

3) Experimental results (FIGS. 3 and 4)

Open field test (FIG. 3): Moving distance in an unfamiliar planar space was compared between the old mice and the young mice. Although the old mice tended to exhibit lower locomotor activity, the difference was statistically insignificant (One Way ANOVA, $p=0.32$). An indicator of the tendency toward anxiety, i.e., time of stay in the central portion, decreased significantly in the old mice compared with the young mice (One way ANOVA with Tukey's post hoc test, $p<0.001$), demonstrating an increased tendency toward anxiety. When ManNAc was administered to the old mice, this rise in the tendency toward anxiety tended to decrease slightly, but the difference was statistically insignificant.

Place task and object task (FIG. 4): In the young mice (FIG. 4B), in the place recognition task ("Place" in FIG. 4B), exploration time for an object placed at a new place extended significantly (paired t-test, $p<0.05$), demonstrating that the mice were able to recognize and memorize the change of the place. In the object recognition task ("object" in FIG. 4B), exploration time for a new object ("New" in FIG. 4B) extended (paired t-test, $p<0.001$), demonstrating that the mice were able to recognize and memorize the change of the object. In the old mice (FIG. 4A), in both tests, exploration times for a new place (paired t-test, $p=0.72$) and a new object (paired t-test, $p=0.94$) did not extend; disturbances of these recognition tasks were detected. When ManNAc was administered to the old mice (FIG. 4C), the exploratory behavior times for the new place (paired t-test, $p<0.05$) and the new object (paired t-test, $p<0.001$) normalized in all tasks; a capability of recognition memory equivalent to that of the young mice was shown.

Comprehensively judging from these results of the open field test, place task and object task, it is evident that. ManNAc improves place memory and object memory without influencing total motor activity.

Example 2

Recovery from Aging-Related Sleep Disorders Using ManNAc

Mice are awake during active time in the dark phase and conversely cease their activities and have a sleep in the light phase. It is known that in aged mice, the wake-sleep rhythm is deranged to the extent of lighter sleep in the light phase and decreased activities during wake time in the dark phase. It is also known that the aging-related derangement of wake and sleep is related to hypothalamic activity and accompanied by elevated body temperatures and increased heart rates. Because these symptoms are similar to those in human patients in their middle age to senescence who complain of dissatisfaction with sleep, they serve as an appropriate model for examining the influences on sleep.

Middle-aged mice [three reared from 43 to 66 weeks of age under light-dark cycle conditions (12-hour light phase-12-hour dark phase)] were allowed to drink ManNAc solution (5 mg/ml tap water) ad libitum. During 1 week before and after the free access to the solution, respiratory rate, body temperature, and locomotor activity were monitored over time using a telemeter. Also analyzed were electroencephalograms recorded during wake and sleep times in both the ManNAc non-ingestion period and the free-access period. To measure electroencephalograms and electromyograms, a mouse electroencephalogram transmitter (F20EET, Data Sciences) was implanted in each animal under anesthesia (pentobarbital, 30 mg/kg, i.v.), and electroencephalograms, electromyograms, body temperature, and locomotor activity were continuously recorded using ART (Data Sciences Company). The electroencephalograms thus obtained were analyzed using Neuro-Score (Data Sciences Company), and the sleep events were classified into REM sleep and slow wave sleep. The lengths of each sleep stage were totaled and compared among the mice before and after administration and young mice.

Figure 5:
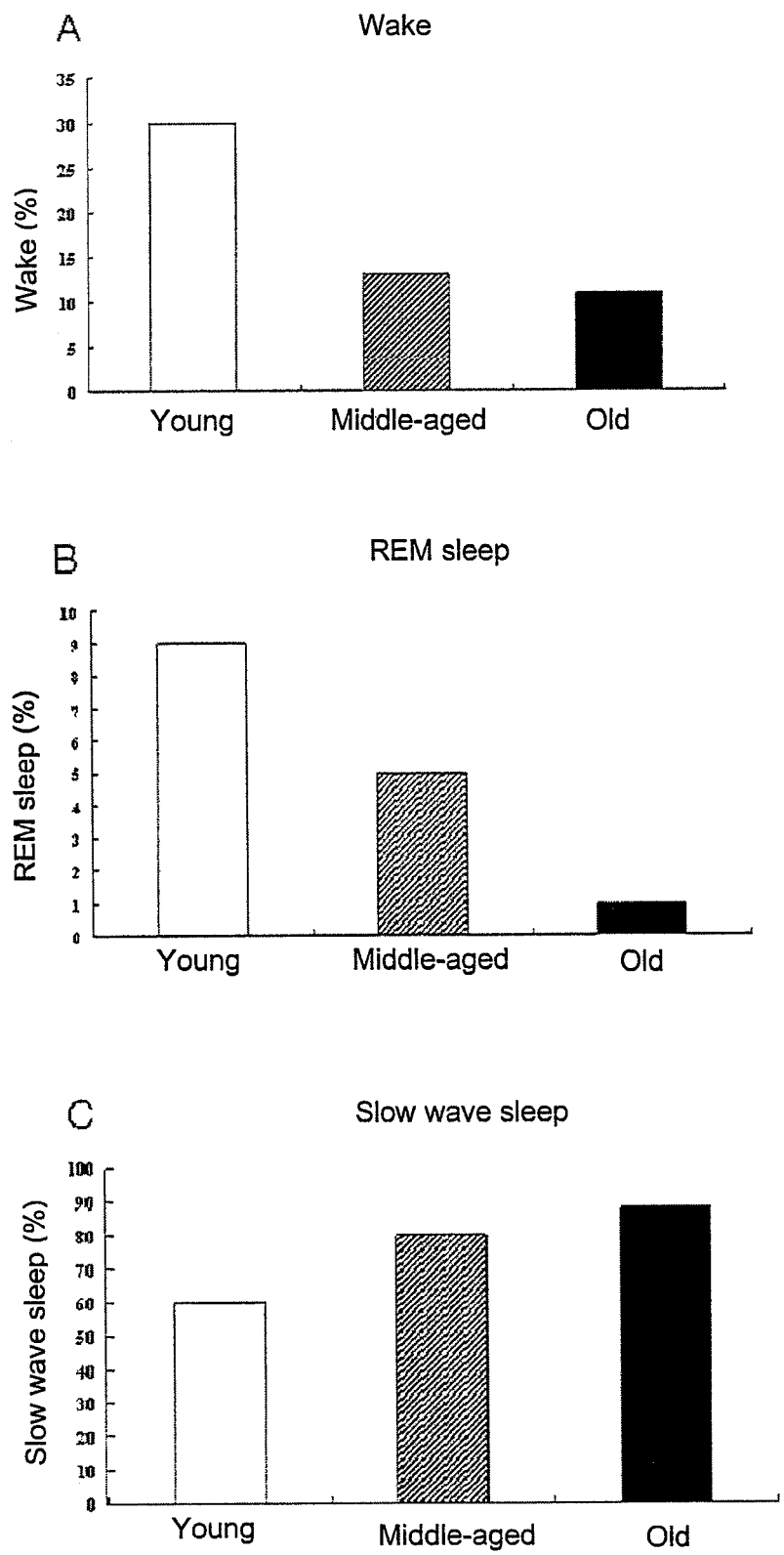
FIG. 5 is a graphic representation of the influences of age on sleep and wake stages using young, middle-aged and old mice.

Analysis of pre-administration period confirmed decreased wake time, decreased REM sleep, and increased slow wave sleep in the old mice (43 to 55 weeks of age) compared with the young mice (17 to 21 weeks of age) (FIG. 5).

Figure 6:
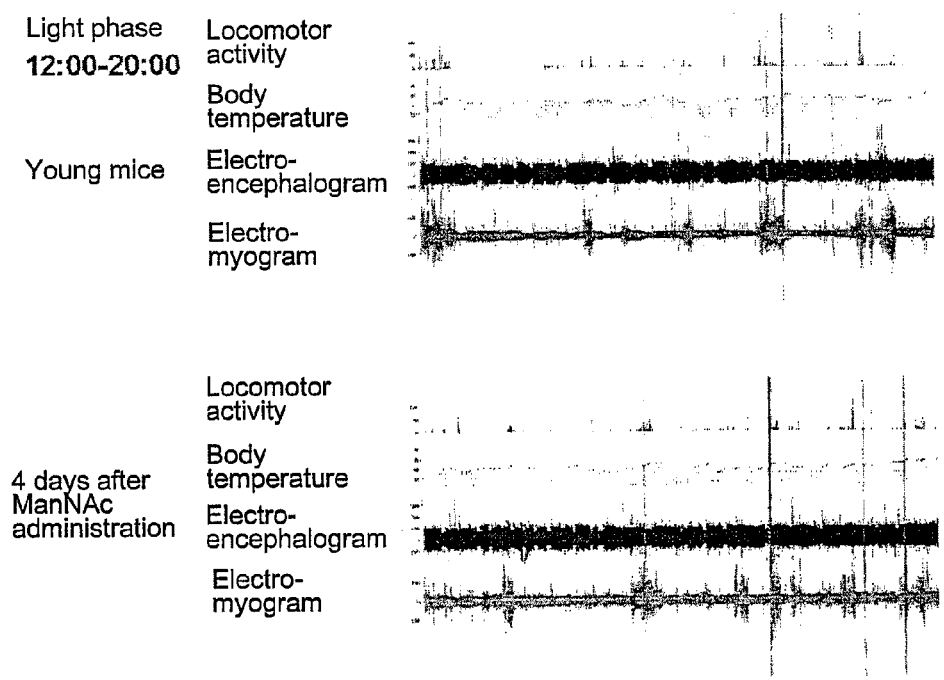
FIG. 6 shows the results of measurements of locomotor activity, body temperature, electroencephalograms and electromyograms in young mice and in middle-aged mice receiving N-acetyl-D-mannosamine (ManNAc), in the light phase (12:00-20:00).
Figure 7:
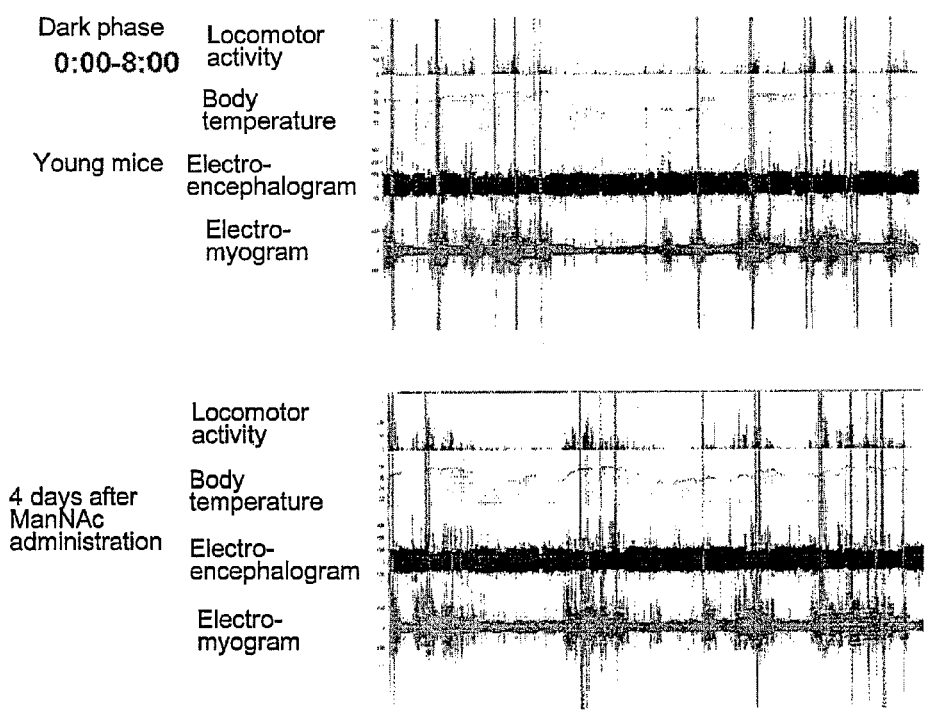
FIG. 7 shows the results of measurements of locomotor activity, body temperature, electroencephalograms and electromyograms in young mice and in middle-aged mice receiving N-acetyl-D-mannosamine (ManNAc), in the dark phase (0:00-8:00).
Figure 8:
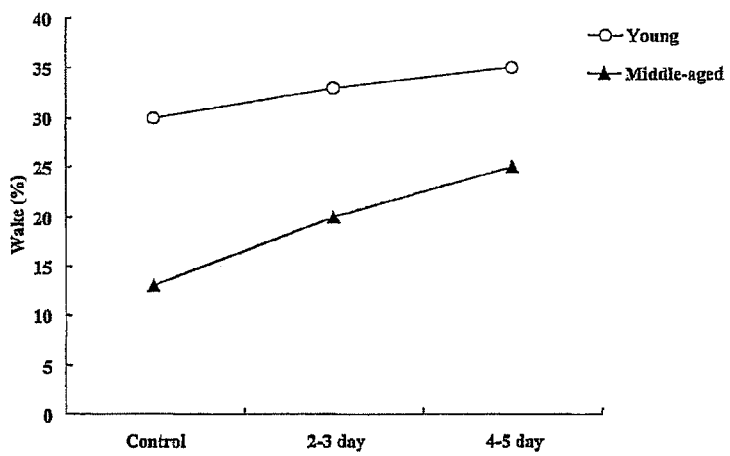
FIG. 8 is a graphic representation of the influences of administration of N-acetyl-D-mannosamine on wake, REM sleep and slow wave sleep in young mice and middle-aged mice.
Figure 8:
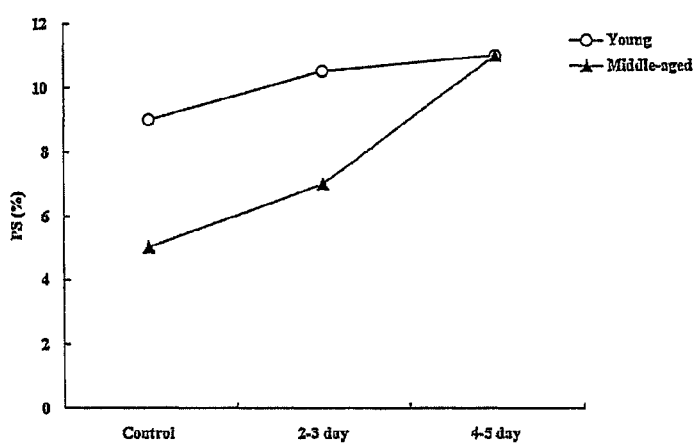
Figure 8:
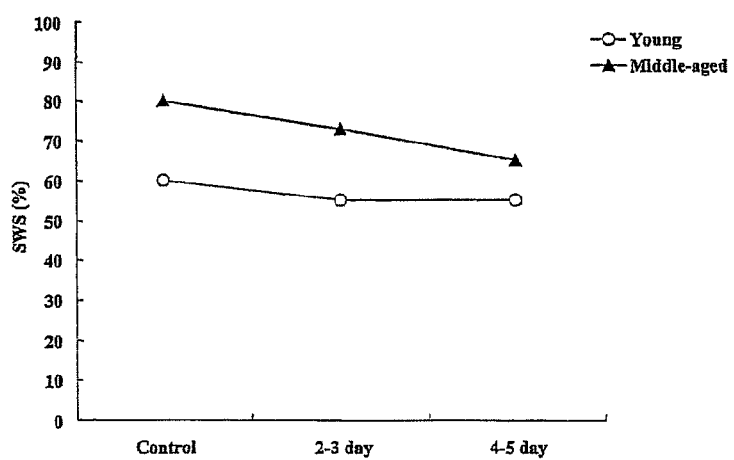

The electroencephalograms, electromyograms, body temperature, and locomotor activity during the light phase (non-active phase: mice are nocturnal) and the dark phase (active phase) in the middle-aged mice obtained on day 4 after administration are shown graphically. For control, electroencephalograms, electromyograms, body temperature, and locomotor activity in the young mice are likewise shown graphically (FIGS. 6 and 7). In the middle-aged mice receiving ManNAc, remarkably increased wake time, increased REM sleep, and decreased slow wave sleep began to be observed on day 2 to after administration (FIG. 8, Table 1).

TABLE 1

| Type | Sleep analysis results (daily percentage) | |
| --- | --- | --- |
| | Before administration (%) | 4 days after administration (%) |
| Wake | 1.8 | 2.2 |
| Wake (major) | 12.7 | 15.3 |
| REM sleep | 5.4 | 10.0 |
| Slow wave sleep | 80.0 | 72.5 |

Figure 9:
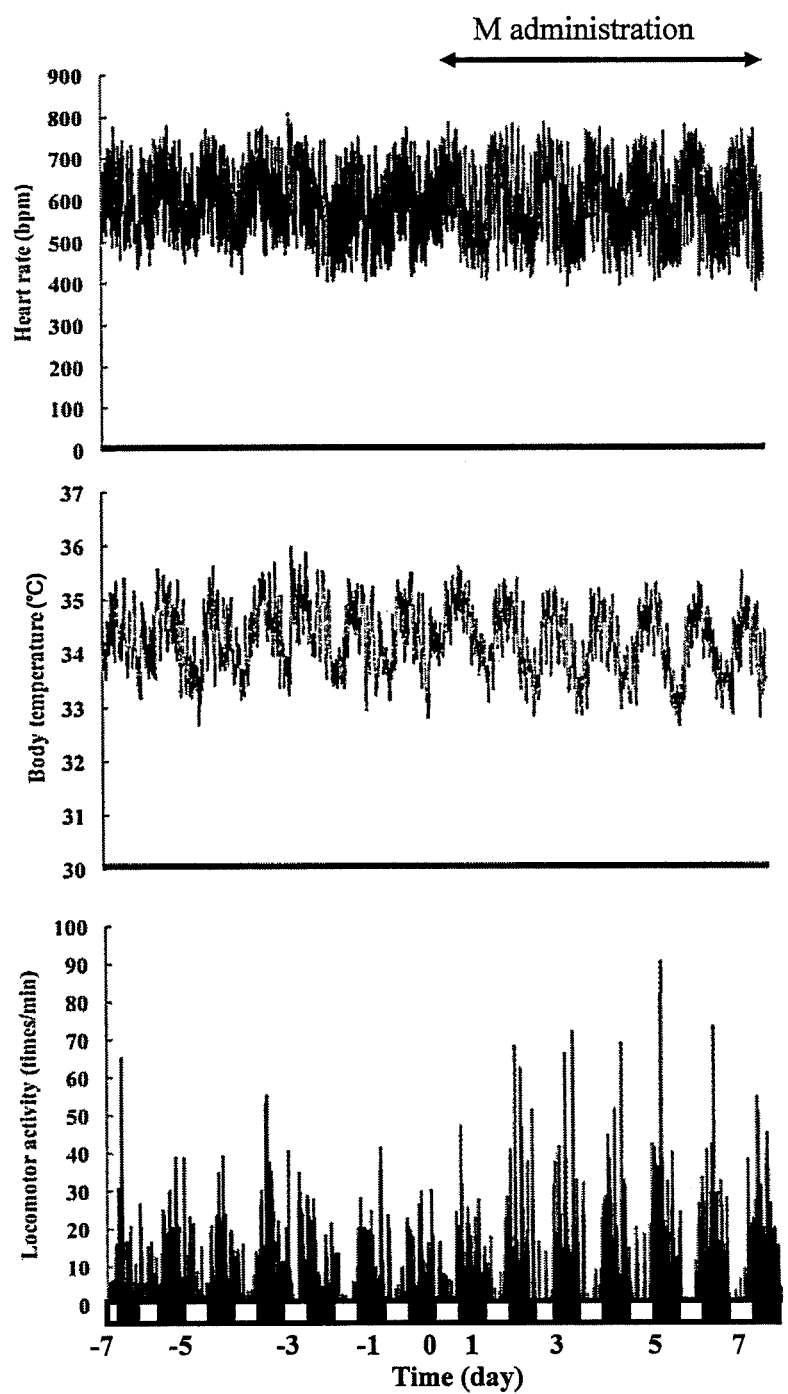
FIG. 9 shows the results of measurements of heart rate, body temperature and locomotor activity in an experiment of recovery from aging-related sleep disorders, wherein M administration indicates duration of administration of N-acetyl-D-mannosamine.

Furthermore, administration of ManNAc increased the difference in locomotor activity between the light and dark phases (FIG. 9). With administration of ManNAc, the change in heart rate due to behavioral change, i.e., the difference between the light and dark phases, became evident, whereas body temperature declined during the non-active period. These results show that ManNAc improves both the quality and quantity of sleep, and is hence remarkably effective in inducing wake-sleep rhythmic cycle between day and night, demonstrating that ManNAc serves as an effective ingredient for a sleep improver.

INDUSTRIAL APPLICABILITY

By taking or eating a medicament or food provided by the present invention, which contains ManNAc as an active ingredient, aging-related brain hypofunction can be prevented, ameliorated or treated. Taking or eating a medicament or food of the present invention also makes it possible to prevent, ameliorate or treat REM sleep disorders, whereby an improvement of the quality of sleep is expected.

The invention claimed is:

1. A method of ameliorating or treating a disorder due to a brain hypofunction selected from the group consisting of memory disorders and decrease in motor function, comprising the step of administering an effective amount of N-acetyl-D-mannosamine to a subject in need thereof, thereby ameliorating or treating the disorder.

2. The method according to claim 1, wherein the memory disorders are selected from the group consisting of place memory disorders and object memory disorders.

3. A method of ameliorating a brain hypofunction selected from the group consisting of memory disorders and decrease in motor function, comprising the step of allowing an effective amount of N-acetyl-D-mannosamine to be taken by a subject in need thereof, thereby ameliorating the brain hypofunction.

4. The method according to claim 3, wherein the memory disorders are selected from the group consisting of place memory disorders and object memory disorders.

5. The method according to claim 4, wherein the memory disorder is a place memory disorder.

6. The method according to claim 4, wherein the memory disorder is an object memory disorder.

7. The method according to claim 2, wherein the memory disorder is a place memory disorder.

8. The method according to claim 2, wherein the memory disorder is an object memory disorder.

* * * * *